United States Patent [19]

Nordling

[11] 4,441,498

[45] Apr. 10, 1984

[54] PLANAR RECEIVER ANTENNA COIL FOR PROGRAMMABLE ELECTROMEDICAL PULSE GENERATOR

[75] Inventor: Neal F. Nordling, White Bear Lake, Minn.

[73] Assignees: Cardio-Pace Medical, Inc., St. Paul, Minn.; Cardio-Pace Medical, Inc., St. Paul, Minn.

[21] Appl. No.: 376,300

[22] Filed: May 10, 1982

[51] Int. Cl.³ .............................................. A61N 1/36
[52] U.S. Cl. ......................... 128/419 P; 128/419 PG; 128/903
[58] Field of Search ............. 128/419 P, 419 PG, 903, 128/904, 905; 343/844, 855, 867

[56] References Cited

U.S. PATENT DOCUMENTS

| 2,266,262 | 12/1941 | Polydoroff | 250/33 |
|---|---|---|---|
| 3,631,499 | 12/1971 | Turner | 343/701 |
| 3,683,389 | 8/1972 | Hollis | 343/788 |
| 3,773,051 | 11/1973 | Holcomb et al. | 128/422 |
| 4,010,760 | 3/1977 | Kraska et al. | 128/419 |
| 4,082,097 | 4/1978 | Mann et al. | 128/419 |
| 4,118,693 | 11/1978 | Novikoff | 340/572 |
| 4,143,661 | 3/1979 | LaForge et al. | 128/419 |
| 4,166,470 | 9/1979 | Neumann | 128/419 |
| 4,220,156 | 9/1980 | Schulman et al. | 128/419 |
| 4,304,237 | 12/1981 | Mensink | 128/419 |
| 4,304,238 | 12/1981 | Fischer | 128/419 |
| 4,361,153 | 11/1982 | Slocum et al. | 128/419 P |

OTHER PUBLICATIONS

Radio-Frequency Pacemaker w/ Receiver Coil Implanted on Heart, Camilli et al.—Annals of NY Acad. of Science.
Portable Mini Transistorized R-F Coupled Cardiac Pacemaker, Hilkman et al.—IRE Trans. on Bio-Med Elec.

Primary Examiner—Lee S. Cohen
Assistant Examiner—Steven Falk
Attorney, Agent, or Firm—Kinney & Lange

[57] ABSTRACT

An implantable programmable pulse generator provides electrical stimulation signals to the heart of a patient. The operating parameters of the pulse generator, such as stimulation rate, refractory period duration, and operating mode are programmable by a physician after the pulse generator has been implanted surgically in the patient. An external programmer device includes a transmitter of coded radio frequency (RF) signals. The pulse generator includes a receiver antenna for receiving the coded RF signals. The receiver antenna includes a first wire-wound, air core, planar coil antenna carried on a flexible insulating substrate adjacent an inner wall of a first major side surface of the pulse generator housing and a second wire-wound, air core, planar coil antenna carried on the flexible insulating substrate adjacent an inner wall of a second major side surface of the pulse generator housing. The planar coils are series additive connected to the programmable pulse generator circuit so that the RF signals will be received regardless of the orientation of the pulse generator when it is implanted in the patient. The planar receiver coil antenna provides reliable reception of the RF signal even when the transmitter coil of the programmer is slightly misaligned or tilted with respect to the receiver coil antenna. In addition, the antenna provides a shallow Q factor so that individual high tolerance tuning of the receiver circuits of the pulse generator is not required.

5 Claims, 5 Drawing Figures

PLANAR RECEIVER ANTENNA COIL FOR PROGRAMMABLE ELECTROMEDICAL PULSE GENERATOR

BACKGROUND OF THE INVENTION

1. Field of the Invention.

The present invention relates to electronic devices which are implantable within the human body, such as cardiac stimulating pulse generators. In particular, the present invention is related to an improved receiver antenna for use in a programmable pulse generator.

2. Description of the Prior Art.

One important advance in health care and medical technology over the past several decades has been the development of implantable electromedical pulse generators which provide electrical stimuli to the heart or to other organs. Implantable pulse generators now find common use as heart pacemakers which are typically implanted within the chest beneath the patient's skin and which provide electrical pulse stimuli to the heart via one or more flexible leads. An electrode at the distal tip of the lead normally contacts heart tissue to supply the electrical pulse stimulation from the pulse generator.

Programmable heart pacemakers have been developed which allow a physician to change operating parameters of the pacemaker after it has been implanted. For example, the physician may wish to alter the stimulation rate of the pacemaker from that which was set at the time the pacemaker was implanted; may wish to alter the refractory period duration; or may wish to vary the mode of operation of the pacemaker from an R wave inhibited demand mode to an asynchronous mode, or vice versa.

To accommodate the need for altering operating parameters of a pacemaker after it has been implanted, programmable pacemakers have been developed. The physician uses an external programmer unit which provides a magnetic or electromagnetic signal. The programmer is placed over the patient's skin where the pacemaker has been implanted, and reprogramming signals are transmitted to the pacemaker. In one common type of programmable pacemaker, a magnetically actuated reed switch is contained within the pacemaker for receiving the magnetic or electromagnetic signals from the programmer.

While a reed switch meets the physical size restrictions for use in a pacemaker, its inherent slow response limits the rate at which reprogramming signals can be transmitted from the programmer to the pacemaker. In a pacemaker in which several different operating parameters can be programmed, the slow rate of transmission of information from the programmer to the pacemaker necessitated by a reed switch is highly undesirable.

An alternative to the reed switch as a receiver in a programmable pacemaker is an antenna small enough to fit within the housing of the pacemaker. Small antennas can, however, exhibit limited distance response, high directivity, and high sensitivity to axial misalignment between the axis of the transmitter coil and the axis of the antenna. This can make proper positioning and orientation of the pacemaker during implantations as well as proper positioning of the programmer unit over the implanted pacemaker during use very critical.

There is a continued need for improved programmable pulse generators, including pacemakers, which are highly insusceptible to electromagnetic noise, will reliably receive signals from the programmer and will reprogram the pulse generator operating parameters even when the pulse generator is slightly misaligned or tilted with respect to the implanted pulse generator, and do not require extensive and difficult to tune, receiver circuitry.

SUMMARY OF THE INVENTION

The present invention is an improved implantable programmable electromedical pulse generator which has programmable operating parameters based upon encoded radio frequency (RF) signals from a transmitter located outside the body of the patient. The pulse generator includes a hermetically sealed housing within which a battery, programmable pulse generator circuit means, and planar receiver coil means are located. The programmable pulse generator circuit means is powered by the battery and is connected to the planar receiver coil means for producing an electrical pulse signal based upon programmable operating parameters which are determined by RF signals received by the planar receiver coil means.

In the programmable pulse generator of the present invention, the planar receiver coil means is positioned within the housing adjacent an inner wall of the housing. In preferred embodiments of the present invention, the planar receiver coil means preferably includes first and second wire-wound air core, planar receiver coil antennae which are positioned respectively adjacent opposite generally parallel side walls of the housing, so that RF signals are received regardless of which major side surface of the implanted pulse generator is closest to the skin of the patient.

The planar receiver coil means preferably includes a flexible insulating substrate having a first zone which carries the first planar receiver coil antenna and a second zone which carries the second planar receiver coil antenna. The flexible substrate has a third zone which connects the first and second zone.

DETAILED DESCRIPTION OF THE PREFERRED EMBODIMENTS

Figure 1:
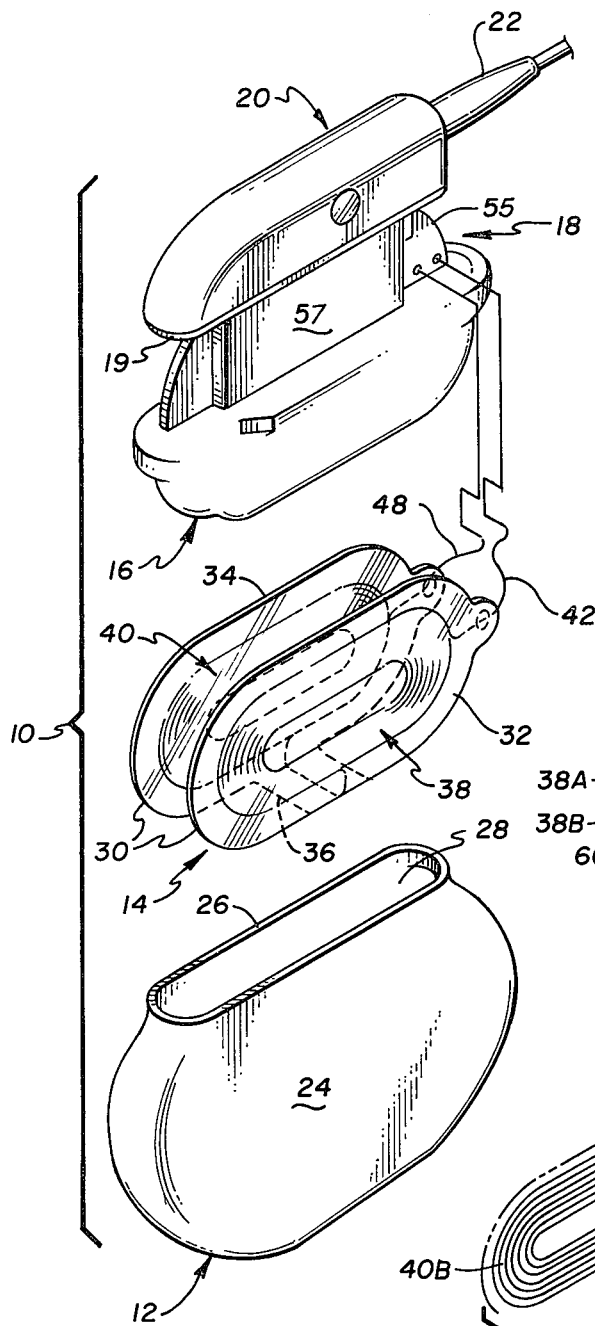
FIG. 1 is an exploded pictorial view of an implantable pulse generator of the present invention including the planar receiver coil assembly and illustrating the relative position of the receiver coil assembly with respect to other parts of the pacemaker.

FIG. 1 shows in exploded view a small, lightweight, programmable implantable pulse generator 10 which embodies the present invention. Pulse generator 10 includes titanium housing or cannister 12, planar receiver coil assembly 14, lithium iodide battery 16, pulse generator circuitry 18, metallic top cover 19 and epoxy top 20. In FIG. 1, a portion of conductive lead 22 is shown connected to pulse generator 10. Lead 22 is a flexible insulated electrical conductor which carries a stimulating electrical impulse from pulse generator 10 to the heart of the patient.

As illustrated in FIG. 1, titanium housing 12 has a pair of major side walls 24 and 26 which are generally flat, parallel to one another, and relatively closely spaced. Receiver coil assembly 14, battery 16, and circuitry 18 all are positioned between side walls 24 and 26 of housing 12 when pulse generator 10 is in assembled condition. Housing 12 has an elongated top opening 28 through which receiver coil assembly 14, battery 16 and circuitry 18 are inserted during assembly of pulse generator 10. Top cover 19 is placed over opening 28, and the contents of housing 12 are hermetically sealed within housing 12 to isolate the components (particularly circuitry 18) from damage due to body fluids of the patient.

Receiver coil assembly 14 includes flexible multilayer electrically insulating substrate 30, which assumes a general U-shaped configuration when coil assembly 14 is positioned within housing 12. Substrate 30 includes a first zone 32 which is positioned adjacent the inner wall of first side wall 24, a second zone 34 which is positioned adjacent the inner surface of second side wall 26 of housing 12, and a third zone 36 which connects first and second zones 32 and 34 and which is positioned near the bottom of the interior of housing 12. The resilient properties of substrate 30 tend to cause zones 32 and 34 to be urged outward and away from one another toward a flat configuration like that shown in FIG. 2. As a result, the resilient characteristic of flexible substrate 30 with zone 36 connecting the two major zones 32 and 34 tends to bias zones 32 and 34 outward so that they abut and generally conform to the inner surfaces of side walls 24 and 26 of housing 12.

First zone 32 of substrate 30 carries a first planar, wire-wound, air core receiver coil antenna 38. Similarly, second zone 34 carries a second planar, wire-wound, air core receiver coil antenna 40. As further described with reference to FIGS. 2-4, antenna coil 38 preferably includes a pair of flat superimposed wire-wound coils 38A and 38B which are series additive connected, and antenna 40 similarly includes a pair of flat superimposed wire-wound coils 40A and 40B which are series additive connected. One end 42 of first antenna 38 extends out of hole 44 in tongue 46 of zone 32 and is connected to circuitry 18. Similarly, one end 48 of second antenna 40 extends out of hole 50 in tongue 52 of second zone 34 and is connected to circuitry 18. End 54 of first antenna 38 and end 56 of second antenna 40 are connected together in third zone 36. Windings 38A, 38B, 40A and 40B are series additive wound so that the currents induced in the windings 38A, 38B of antenna 38 and windings 40A and 40B of antenna 40 due to received RF signals are all additive.

During assembly, receiver coil assembly 14 is wrapped around the bottom and sides of battery 16 and circuitry 18 and the entire assembly is then inserted through top opening 28 into housing 12. In a preferred embodiment of the present invention, battery 16 is a Model 7905, 1.7AH lithium iodine battery by Wilson Greatbatch Ltd. Battery 16 has a shape which generally conforms to the lower portion of the interior of housing 12. An insulating cover of a polymeric material (not shown) preferably covers at least a portion of battery 16 and provides further electrical isolation between battery 16 and housing 12.

Circuitry 18 includes a printed circuit board 55 mounted on a top surface of battery 16 and a hermetically sealed hybrid pulse generator circuit 57 which is mounted on circuit board 55. Hybrid circuit 57 is thus doubly hermetically sealed to isolate the circuitry from body fluids of the patient. An electrical block diagram of hybrid circuit 57 will be described in further detail with reference to FIG. 5. When pulse generator 10 is in its fully assembled condition, printed circuit board 55 as well as hybrid circuit 57 are located between zones 32 and 34 of receiver coil substrate 30.

Metallic top cover 19, which is preferably titanium, covers top opening 28 of housing 12 and is welded to housing 12 to provide hermetic sealing. Top cover 19 includes one or more electrical feed throughs (not shown) which extend between and electrically connect hybrid circuit 57 with one or more connector blocks (not shown) within epoxy top 20. One or more leads such as lead 22 shown in FIG. 1 are inserted into and connected to the connector blocks in epoxy top 20.

Pulse generator 10 shown in FIG. 1 is a programmable pulse generator in which operating parameters such as stimulation rate, refractory period duration, and operating mode are programmable by encoded RF signals generated by a programmer outside the patient's body and received by receiver coil assembly 14. An easy-to-use and reliable communication link between pulse generator 10 and the external programmer is essential. If the physician must fumble around to align the two units or must engage in a great deal of trial and error in order to reliably transmit encoded RF signals which are received by pulse generator 10, the advantages of a programmable pulse generator are reduced.

Receiver coil assembly 14 of the present invention provides a highly advantageous structure for receiving programming signals at high transmission rates. Receiver coil assembly 14 is small in weight and in thickness, and thus is ideally suited for use in an implanted pulse generator. The use of two planar wire-wound air core coil antennas 38 and 40 has several important advantages. First, it allows each receiver coil antenna 38 or 40 to be as large as possible within the physical confines of housing 12. Since coils 38 and 40 are planar, they minimize the need for Z axis centering (i.e. coaxial alignment of coils 38 and 40 with the transmitter coil) and minimize sensitivity to tilt of the receiver coil assembly 14 with respect to the Z axis of the transmitter coil of the programmer. Although a small cylindrical receiver coil could satisfy the physical dimension restrictions of a pacemaker, a cylindrical receiver coil exhibits highly directional properties. If the plane of the transmitter coil is not perpendicular to the axis of a cylindrical receiver coil, or if the center of the Z axis is not in the geometric center of the transmitter coil, maximum flux linkage does not occur. Since the pacemaker is implanted in a patient's body, precise alignment of the programmer in order to maximize flux linkage to a small cylindrical coil would be extremely difficult. Receiver coil assembly 14 of the present invention utilizes a pair of planar receiver coil antennas 38 and 40 to minimize both tilt sensitivity and the need for precise Z axis centering.

Second, by dividing receiver coil assembly 14 into two symmetrical halves (as represented by coil antennas 38 and 40), equal reception of RF programmer signals will be achieved regardless of whether side 24 or side 26 of housing 12 is nearest the outside of the patient's body. Thus the physician implanting pacemaker 10 does not have to worry about aligning pacemaker 10 in only one particular orientation during the surgery.

Third, receiver coil assembly 14 utilizes planar coils with an air core dielectric, which avoids collapse of the electromagnetic field. The planar configuration of receiver coil assembly 14 of the present invention allows the air core to be as large as possible within the physical size and shape constraints of housing 12.

Figure 2:
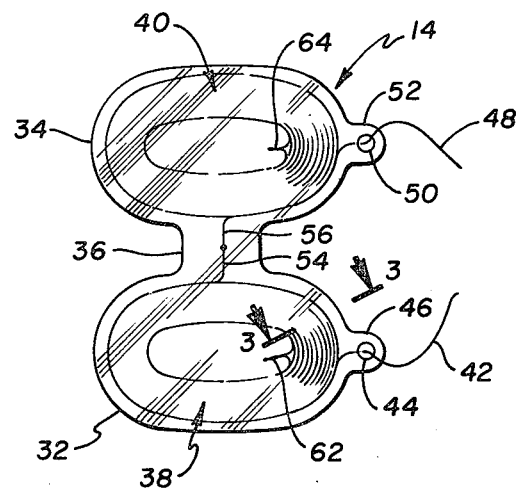
FIG. 2 is a plan view of the receiver coil assembly of FIG. 1 in flattened out form.
Figure 3:
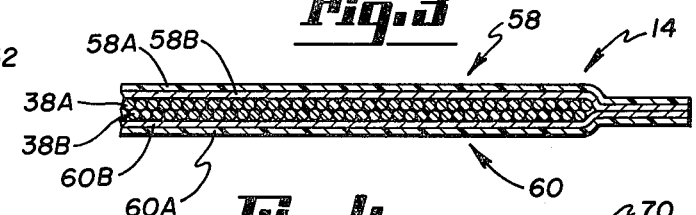
FIG. 3 is a cross-sectional view taken along line 3—3 of FIG. 2 at a greatly enlarged scale.
Figure 4:
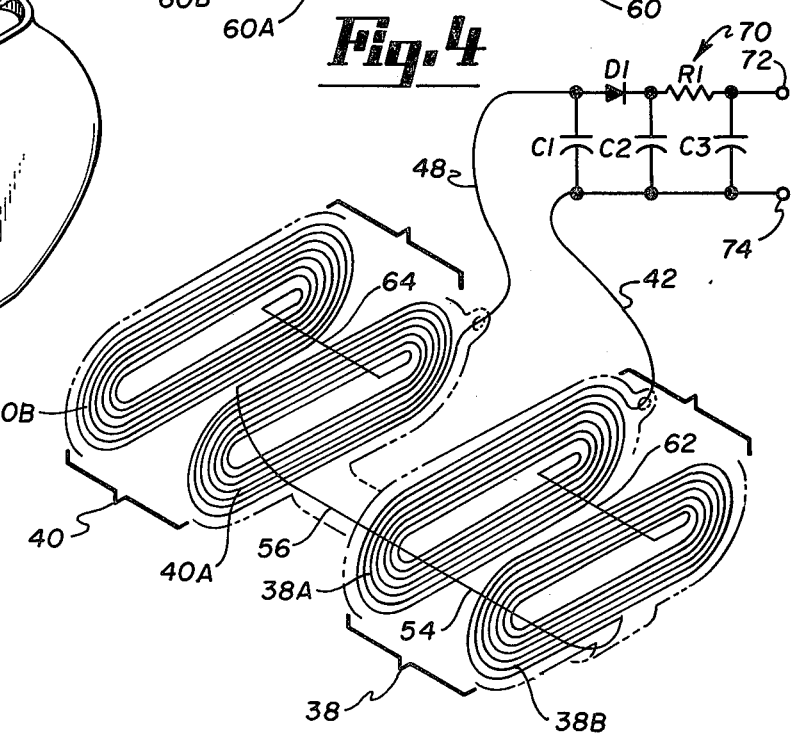
FIG. 4 is a schematic illustration partially in exploded isometric form and partially in electrical schematic form of the winding of the planar receiver coil assembly of FIG. 1 together with receiver circuitry connected to the coil assembly.

The construction of receiver coil assembly 14 of the present invention is shown further in FIGS. 2, 3 and 4. In a preferred embodiment, receiver coil antenna 38 includes a pair of superimposed planar wire-wound coils 38A and 38B which are stacked on top of one another. Similarly, receiver coil antenna 40 is a pair of superimposed planar wire-wound coils 40A and 40B. In the flattened out stage shown in FIG. 2, coil 38A is stacked on top of coil 38B and coil 40A is stacked on top of coil 40B. Coils 38A, 38B, 40A and 40B are sandwiched between top sheet 58 and bottom sheet 60 which form substrate 30. In a preferred embodiment of the present invention, the wire forming coils 38A, 38B, 40A and 40B is 38-gauge, (American wire) having a diameter of 0.004 inches. Each individual planar coil 38A, 38B, 40A and 40B has a total of 65 turns. Each sheet 58 and 60 is preferably a polyimide film 58A, 60A such as Kapton with an adhesive coating 58B, 60B on its inner surface, respectively. The overall thickness of sheets 58 and 60 with coils 38A and 38B and coils 40A and 40B bonded therebetween is 0.016 inch. The polyimide film is highly advantageous because it is puncture resistant and heat resistant. The puncture resistance of polyimide film provides protection to the coils 38A, 38B, 40A and 40B during insertion of receiver coil assembly 14 in housing 12. The heat resistance is important since the upper end of receiver coil assembly 14 is near top cover 19, and thus can be subjected to some of the heat produced during welding of top cover 19 and housing 12. Coils 38A, 38B, 40A and 40B are thus sealed between sheets 58 and 60 to provide protection as well as maintaining the shape of the coils 38A, 38B, 40A and 40B when antenna assembly 14 is inserted in housing 12.

In the flattened configuration shown in FIG. 2, upper coil 38A is wound inward from end 42 in a clockwise direction. A solder joint 62 connects the inner end of upper coil 38A with the inner end of lower coil 38B. Lower coil 38B is wound in the clockwise direction outward from solder joint 62 to its outer end 54, so that both coils 38A and 38B are wound in the same direction. Outer end 54 of bottom coil 38B is connected to outer end 56 of lower coil 40B in the connecting region 36 between regions 32 and 34 of substrate 30. Lower coil 40B is wound in a counterclockwise direction inward from outer end 56. A solder joint connection 64 connects the inner end of lower coil 40B with the inner end of top coil 40A. Top coil 40A is wound outward in a counterclockwise direction until outer end 48 extends through wire port hole 50 in tab 52. Both coil 40A and coil 40B are, therefore, wound in the same direction.

When receiver coil assembly 14 is folded into its normal operating configuration like that shown in FIGS. 1 and 4, coils 38A and 40A face the interior of housing 12, while bottom coils 38B and 40B face the inner walls of housing 12. The windings of coils 38A, 38B, 40A and 40B, in this folded configuration, are all wound in the same direction and are connected in a series additive relationship. As a result, any magnetic field which passes through both antenna 38 and antenna 40 will induce signals in coils 38A, 38B, 40A and 40B which are additive. FIG. 4 shows, in schematic form, the series additive connections of coils 38A, 38B, 40A and 40B when receiver coil assembly 14 is in its folded configuration.

As shown in FIG. 2, ends 42 and 48 of the coils exit from between insulator sheets 58 and 60 through port holes 44 and 50 in tabs 46 and 52, respectively, of sheet 58. Holes 44 and 50 are positioned so that they face inward toward one another when receiver coil assembly 14 is in its folded configuration. Tabs 46 and 52, therefore, provide protection to wire ends 42 and 48 against rubbing and shorting against the inner walls of housing 12 during insertion of receiver coil assembly 14 into housing 12.

Another important characteristic of the receiver coil assembly 14 of the present invention is that a shallow Q factor should be achieved. This relaxes electrical component value tolerances in the tuning of the receiver circuitry. This has the important advantage of not requiring individual hand tuning of each receiver circuit.

FIG. 4 also illustrates in electrical schematic form the receiver circuit used in conjunction with receiver coil assembly 14. Receiver circuit 70 includes capacitor C1 which is connected between wires 42 and 48, Schottky detector diode D1, capacitor C2, resistor R1, and capacitor C3. Detector diode D1 has its anode connected to wire 48 and its cathode connected to one terminal of capacitor C2 and one terminal of resistor R1. The opposite terminal of capacitor C2 is connected to wire 42. Resistor R1 is connected between the cathode of diode D1 and output terminal 72. Capacitor C3 is connected between output terminal 72 and output terminal 74. As shown in FIG. 4, wire 42 is also connected to output terminal 74. The properties of coil assembly 14 and receiver circuit 40 are designed to be tuned near a frequency of 262.5 KHz, which is the transmitting frequency of the programmer. In the preferred embodiment one-half or the other of receiver coil assembly 14 is normally shielded from the incoming RF signals by battery 16 and the hybrid circuit 57. The properties of one pair of the coils 38A, 38B or 40A, 40B, therefore, determines the detecting properties.

In a preferred embodiment, capacitor C1 has a capacitance of about 1,000 pf, C2 has a capacitance of about 680 pf, C3 has a capacitance of about 1,000 pf, and resistor R1 has a resistance of 20 Kohms. This results in a Q factor of about 27, with resonance of about 230 KHz. Schottky detector diode D1 is operated in a zero bias mode, and provides low junction voltage drop losses. The resistance of receiver coil assembly 14 is small compared to the video resistance of Schottky detector diode D1.

Testing of this preferred embodiment with an 8-volt battery in the programmer yielded a 20 mv signal when the programmer was 3.25 inches away from front surface 24 of housing 12. A 20 mv signal was also produced when the programmer was 2.63 inches from rear surface 26 of housing 12. This is excellent sensitivity, since in normal use the programmer is not expected to be more than 2 inches from either surface 24 or 26, depending upon the orientation of pulse generator 10 in the patient's body. In addition, testing of this preferred embodiment demonstrated that receiver coil assembly 14 within pulse generator 10 was relatively insensitive to location and tilt variations of the programmer with respect to pulse generator 10.

Figure 5:
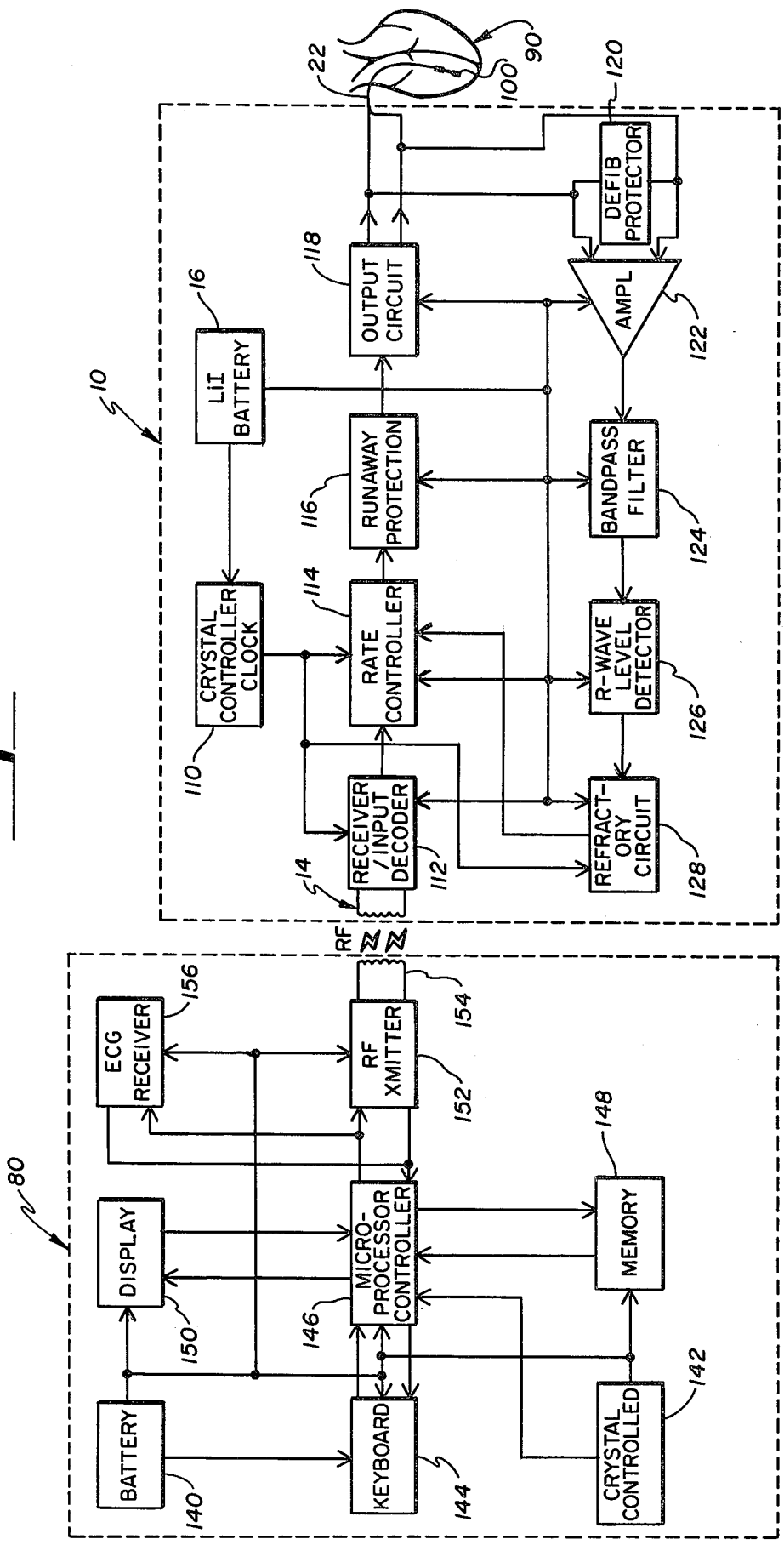
FIG. 5 is an electrical block diagram illustrating a programmable pulse generator which utilizes the receiver coil assembly of the present invention, together with an electrical block diagram of a programmer which supplies encoded RF signals which are received by the receiver coil assembly for reprogramming operating parameters of the pulse generator.

FIG. 5 is an electrical block diagram of pulse generator 10 and programmer 80. As shown in FIG. 2, pulse generator 10 is an implantable programmable ventricular pulse generator which provides electrical pulses to heart 90 of a patient through one or more leads 22. In the diagram contained in FIG. 2, electrode 100 at the distal end of lead 22 is shown placed within heart 90.

Pulse generator 10 is powered by lithium iodine battery 16, which is preferably a long-life battery developed for use in implantable prosthetics. The timing reference to all electrical circuitry within pulse generator 10 is provided by crystal controlled clock 110, which is powered by battery 16 and which preferably includes a quartz crystal. Crystal controlled clock 110 provides a timing reference that is stable at both room temperature and body temperature and from the battery voltage present at "beginning of life" to the battery voltage present at a preselected "elected replacement time". Because of this stability, the parameters of pulse generator 10 remain stable and predictable.

Receiver/input decoder 112 acts as a communication interface with programmer 80. As shown in FIG. 2, receiver/input decoder 112 receives signals from receiver coil assembly 14 and includes the receiver circuit 70 which is shown in FIG. 4. Receiver/input decoder 112 and rate controller 114 monitor the coded data received from programmer 80 through receiver coil assembly 14 and check the coded data to ensure that it originated from programmer 80 and from no other source of RF energy. If the coded data is in fact coming from programmer 80, pulse generator 10 is programmed to the desired operating parameters.

Run-away protection circuit 116 is independent of the basic pacing rate circuitry of pulse generator 10. In the preferred embodiment, run-away protection circuit 116 limits the pulse rate of the output signal supplied through lead 22 to heart 90 to approximately 145 ppm. In the event the circuitry of pulse generator 10 tries to exceed the 145 ppm pulse rate, run-away protection circuit 116 causes the pulse rate of pulse generator 10 to revert automatically to approximately 72.5 ppm.

Output circuit 118 provides the needed pulse energy to stimulate heart 90. Output circuit 118 generates a 5-volt pulse that is transmitted via electrode 100 to heart 90 for stimulation.

Debrillation protector 120 is connected to electrode 100 to protect pulse generator 10 from electrical damage during debrillation procedures.

Pulse generator 10 uses amplifier 122 to amplify electrical signals present on electrode 100. The human R wave is normally of very small amplitude, somewhere in the range of 2 to 30 mv. This small signal is amplified by amplifier 122 so that it can be processed through the circuitry of pulse generator 10 to allow pulse generator 10 to operate in an R wave inhibited demand mode of operation.

Band pass filter 124 receives the output of amplifier 122, and prevents the circuitry of pulse generator 10 from falsely interpreting electrical noise as human heart signals. Band pass filter 124 acts as a signal discriminator which attenuates unwanted signals (EMI, T waves, etc.), but which passes signals containing fundamental frequency components of R waves. Thus, band pass filter 124 stops most unwanted signals and passes most normal electrical activities of heart 90. In a preferred embodiment, band pass filter 124 has a center frequency of about 22 Hz with a 3 db band width of between 10 Hz and 150 Hz.

The R wave sensing circuitry of pulse generator 10 includes amplifier 122, band pass filter 124, and R wave level detector 126. Amplifier 122 amplifies the electrical signals presented to pulse generator 10 via leads 22. Band pass filter 124 acts as a signal discriminator, passing signals containing the fundamental frequency of an R wave and attenuating all other signals. Level detector 126 further assesses the signal processed through band pass filter 124 to ensure that it is of sufficient amplitude.

The output of R wave level detector 126 is supplied to refractory circuit 128, which provides a programmable refractory period. A standard refractory period of 310 ms and an extended refractory period of 405 ms are programmable by means of programmer 80.

The refractory period is the same after both sensed and paced beats. The refractory period is composed of an absolute and a relative component. During the absolute refractory period the circuitry of pulse generator 10 will ignore all signals present on leads 22. During the relative refractory period the R wave sensing circuitry will sense signals present on leads 22, but will not allow pulse generator inhibition.

If noise (EMI) of sufficient amplitude to be sensed is present, the relative refractory period will extend, and the pulse generator will revert to an asynchronous mode until the noise ceases.

In the preferred embodiments shown in FIG. 5, pulse generator 10 has several different operating modes. In an inhibited mode, spontaneous ventricular rhythm above the pacing rate of pulse generator 10 (as programmed in rate controller 114 through signals from programmer 80) is sensed by the R wave sensing circuitry. The output of R wave level detector 126 is supplied to refractory circuit 128, which resets timing and inhibits pacing stimuli from being provided to leads 22.

In a pacing mode, when a signal representing a spontaneous QRS complex fails to occur within a preset pacing cycle, pulse generator 10 delivers a pacing stimulus through leads 22 at the programmed rate, and continues to do so until inhibited by one or more natural QRS complexes sensed through the R wave sensing circuit. The stimulus is a biphasic pulse with a nominal 5.0-volt (10.0 ma) output into a nominal 500 ohm load. At a nominal pulse width of 0.65 ms, this provides 32.5 microjoules per pulse into 500 ohms.

In an asynchronous mode, sponaneous ventricular rhythm sensed through R wave sensing circuitry does not reset timing or inhibit production of pacing stimuli.

In a magnetic test mode, pulse generator 10 will operate asynchronously at a programmed rate when a magnet is applied over the unit. The presence of the magnet is sensed by a reed switch (not shown) which is mounted on circuit board 55. The pulse generator will remain at this programmed rate as long as the magnet is present and will revert back to demand operation after the magnet is removed.

Programmer 80 may also be used to test the rate of pulse generator 10. If the patient is being paced, the programmer is held against the implant site, (i.e. over the implanted pulse generator 10) and the pulse generator rate can be read visually after pressing a test button on programmer 80. If the patient is in a sinus rhythm, pulse generator 10 must be programmed to its asynchronous mode through RF signals supplied from programmer 80 to receiver coil assembly 14. The rate is then read after pulse generator 10 is operating in the asynchronous mode. After the rate check has been performed, pulse generator 10 must be reprogrammed to the inhibited mode by appropriate coded RF signals supplied from programmer 80 to receiver coil assembly 14.

Programmer 80 shown in FIG. 5 includes battery 140, crystal control clock 142, keyboard 144, microprocessor controller 146, memory 148, display 150, RF transmitter 152, transmitter coil 154, and ECG receiver 156. Programmer 80 is an external hand-held device which is used to program pacing rate, refractory period and operating mode. In addition, programmer 80 is also used in a test mode to check the pacing rate of pulse generator 10 after implantation.

Battery 140 supplies power to the circuitry of programmer 80. In the preferred embodiment, battery 140 is a 9-volt alkaline battery.

Crystal controlled clock 142 produces clock signals which provide the timing reference for all electrical activity within programmer 80. Clock 142 provides timing control of the data that is transmitted from programmer 80 to pulse generator 10. The accuracy of crystal controlled clock 142 ensures a good communication link between programmer 80 and pulse generator 10.

Keyboard 144 provides an entry system through which input control signals and data can be entered for controlling operation of programmer 80. In a preferred embodiment, keyboard 144 contains numerical keys from 0 to 9 that are used for entering pacing rate in pulses per minute (ppm). Keyboard 144 also contains an ON/CLEAR key, an ASYN/DEM key, a 310/405 key, an OFF key, a TEST key, and a PROG key.

Microprocessor controller 146 includes a microprocessor and associated interface circuitry which provides control and arithmetic functions necessary to transmit and receive information. Microprocessor 146 receives input signals from keyboard 144, RF transmitter 152, and ECG receiver 156, and provides control signals to display 150, RF transmitter 152, and ECG receiver 156. Operation of microprocessor 146 is determined by an operating program stored within memory 148. In the preferred embodiment of the present invention, memory 148 includes a read only memory (ROM) program memory and a random access memory (RAM) data memory.

Display 150, (which in one preferred embodiment is a liquid crystal display) is controlled by microprocessor 146 to display the parameter being programmed, the rate being tested, the battery status, or the unit measurement of the parameter entered. Display 150 under the control of microprocessor 146 provides a physician with a visual display of exactly what parameter value the physician is programming or testing.

Programming information is supplied in the form of RF signals from transmitter coil assembly 154 through programmer 80 to receiver coil assembly 14 of pulse generator 10. The RF signal is encoded before it is sent. Transmitter coil assembly 154 is driven by RF transmitter 152 under the control of microprocessor 146.

In the embodiment shown in FIG. 5, programmer 80 also includes ECG receiver 156 which is used when programmer 80 is in a test mode to allow programmer 80 to measure the rate of an implantable pulse generator 10 via a skin contact electrocardiagram (ECG). This allows the physician a means of checking the pacing rate immediately after programming pulse generator 10 by means of programmer 80. This also allows the physician a means of checking the "elective replacement time" status of implanted pulse generator 10.

Programmer 80 is turned on by pressing the ON/CLR key of keyboard 144. Programmer 80 is turned off by pressing the OFF key on keyboard 144.

In order to program a pacing rate, the physician depresses the ON/CLEAR button to turn on programmer 80, selects the desired pacing rate by depressing the appropriate numerical keys on keyboard 144, places programmer 80 within two inches of the implanted pulse genrator 10, and then depresses the PROG key on keyboard 144. This causes microprocessor 146 to activate RF transmitter 152 to supply coded RF signals from transmitter coil assembly 154 to receiver coil assembly 14. The RF signals received are decoded by receiver/input decoder circuit 112 of pulse generator 10 and are used to program the pacing rate used by rate controller 114.

In order to program either demand or asynchronous mode, the physician depresses the DEM/ASYN key on keyboard 144. The first depression causes display 150 to display "D", which represents the demand mode. A second depression of the DEM/ASYN key causes display 150 to display "A" representing the asynchronous mode. By depressing the PROG key on keyboard 144, the particuar mode being displayed by display 150 is selected. Microprocessor 146 and RF transmitter 152 produce the coded RF signals which are supplied from transmitter coil assembly 154 to receiver coil assembly 114 to select the desired operating mode.

The refractory time is programmable by use of the 310/405 key on keyboard 144. To program refractory time, the physician depresses the 310/405 key either once or twice. If the key is presssed once, a 310 ms refractory period is selected, and this is displayed on display 150. Similarly, if two depressions of the key are made, a 405 ms refractory period is selected and displayed. The physician then places programmer 80 on the patient's chest above implanted pulse generator 10 and depresses the PROG key. This causes the appropriate RF coded signals to be transmitted to receiver coil assembly 14. The signals are decoded by circuit 112 and are used to select the appropriate refractory period.

To test the pacing rate of pulse generator 10, the physician places programmer 80 on the patient's chest so that the electrical contacts (not shown) of ECG receiver 156 contact the patient's skin. Programmer 80 is held over implanted pulse generator 10 long enough to verify the pacing rate. Display 150 displays "TEST" and also displays the pacing rate. The letters PPM are also displayed on display 150 and flash at a rate which corresponds to the pacing rate sensed by ECG receiver 156.

In conclusion, the implantable programmable pulse generator of the present invention provides an easy-to-use and reliable communication link between pulse generator 10 and programmer 80. The planar receiver antenna coil assembly minimizes directionality problems including tilt sensitivity and sensitivity to Z axis centering. Sensitivity up to $2\frac{1}{2}$ to 3 inches from either side of housing 12 is provided. As a result, the physician does not have to maintain a particular orientation of pulse generator 10 when it is implanted.

Although the present invention has been described with reference to preferred embodiments, workers skilled in the art will recognize that changes may be made in form and detail without departing from the spirit and scope of the invention.

What is claimed is:

1. An implantable, programmable, electromedical pulse generator for implanting in a body of a patient to provide an electrical pulse signal to body tissue of the patient via an electrode connected to the pulse generator, the pulse generator having programmable operating parameters based upon radio frequency (RF) signals from a transmitter located outside the patient, the pulse generator comprising:

a hermetically sealed housing having first and second generally parallel side walls and a bottom;

a terminal supported by the housing for connection to the electrode;

a flexible resilient insulating substrate having a first zone, a second zone, and a third intermediate zone which connects the first and second zones, the flexible resilient insulating substrate being bent in a U-shape and being resiliently positioned within the housing with the first zone being resiliently urged into engagement with an inner surface of the first side wall, the second zone being resiliently urged into engagement with an inner surface of the second side wall, and the third intermediate zone being positioned adjacent an inner surface of the bottom of the housing;

a first planar wire-wound air core coil antenna for receiving the RF signals, the first antenna being carried by the first zone of the flexible insulating substrate;

a second planar wire-wound air core coil antenna for receiving the RF signals, the second antenna being carried by the second zone of the flexible insulating substrate, so that the first and second antennae are in generally parallel relationship;

a battery contained within the housing between the first and second zones of the flexible insulating substrate; and programmable pulse generator means connected to the battery, the terminal and the first and second antennae for producing the electrical pulse signal based upon programmable operating parameters determined by the radio frequency (RF) signals received by the first and second antennae, the programmable pulse generator means being contained within the housing between the first and second zones of the flexible insulating substrate.

2. The pulse generator of claim 1 wherein the first and second antennae are series additive connected.

3. The pulse generator of claim 2 wherein the first and second antennae each includes a pair of superimposed, stacked, series additive connected, wire-wound, air core planar coils.

4. The pulse generator of claim 1 wherein the flexible insulating substrate includes first and second flexible insulating sheets, and wherein the first and second antennae are laminated between the first and second insulated sheets.

5. The pulse generator of claim 1 wherein the third intermediate zone carries an electrical connection between the first and second planar receiver coil antennae.

* * * * *